(12) United States Patent
Hernández Herrero et al.

(10) Patent No.: US 11,642,309 B2
(45) Date of Patent: May 9, 2023

(54) AQUEOUS COMPOSITIONS COMPRISING BILASTINE AND MOMETASONE

(71) Applicant: FAES FARMA, S.A., Vizcaya (ES)

(72) Inventors: Gonzalo Hernández Herrero, Vizcaya (ES); Ana Gonzalo Gorostiza, Vizcaya (ES); Neftalí García Domínguez, Vizcaya (ES); Arturo Zazpe Arce, Vizcaya (ES); Pablo Morán Poladura, Vizcaya (ES); Tania González García, Vizcaya (ES)

(73) Assignee: FAES FARMA, S.A., Vizcaya (ES)

( * ) Notice: Subject to any disclaimer, the term of this patent is extended or adjusted under 35 U.S.C. 154(b) by 179 days.

(21) Appl. No.: 16/756,112

(22) PCT Filed: Oct. 15, 2018

(86) PCT No.: PCT/EP2018/078034
§ 371 (c)(1),
(2) Date: Apr. 14, 2020

(87) PCT Pub. No.: WO2019/076798
PCT Pub. Date: Apr. 25, 2019

(65) Prior Publication Data
US 2021/0186869 A1 Jun. 24, 2021

(30) Foreign Application Priority Data
Oct. 16, 2017 (EP) ..................................... 17382686

(51) Int. Cl.
| | | |
|---|---|---|
| *A61K 9/00* | (2006.01) | |
| *A61K 9/10* | (2006.01) | |
| *A61K 31/454* | (2006.01) | |
| *A61K 31/58* | (2006.01) | |
| *A61K 47/38* | (2006.01) | |
| *A61K 47/40* | (2006.01) | |

(52) U.S. Cl.
CPC .............. *A61K 9/0043* (2013.01); *A61K 9/10* (2013.01); *A61K 31/454* (2013.01); *A61K 31/58* (2013.01); *A61K 47/38* (2013.01); *A61K 47/40* (2013.01)

(58) Field of Classification Search
CPC ...... A61K 9/0043; A61K 9/10; A61K 31/454; A61K 31/58; A61K 47/38; A61K 47/40
See application file for complete search history.

(56) References Cited

U.S. PATENT DOCUMENTS

| 5,798,338 A | 8/1998 | Backensfeld et al. |
| 6,197,757 B1 * | 3/2001 | Perrier ..................... A61Q 1/06 514/53 |
| 2006/0045850 A1 | 3/2006 | Namburi et al. |
| 2006/0147537 A1 * | 7/2006 | Heaton ................... A61P 11/00 514/61 |
| 2007/0082870 A1 | 4/2007 | Buchanan et al. |
| 2009/0312724 A1 | 12/2009 | Pipkin et al. |
| 2011/0105450 A1 | 5/2011 | Chapin et al. |
| 2015/0374703 A1 | 12/2015 | Leighton |

FOREIGN PATENT DOCUMENTS

| CN | 2013736098 A | 4/2014 |
| CN | 103784462 A | 5/2014 |
| EP | 1894559 A1 | 3/2008 |
| EP | 3040334 A1 | 7/2016 |
| EP | 3170816 A1 | 5/2017 |
| KR | 20130030606 A | 3/2013 |
| WO | WO2007005491 A1 | 1/2007 |
| WO | WO2016141219 A1 | 9/2016 |

OTHER PUBLICATIONS

English Translation CN103784462A, from google patents, published May 14, 2014 (Year: 2014).*
Szejtli, J., "Medicinal Applications of Cyclodextrins", "Med. Research Reviews", 1994, pp. 353-386, vol. 14, No. 3.

* cited by examiner

*Primary Examiner* — Jeffrey S Lundgren
*Assistant Examiner* — William Y Lee
(74) *Attorney, Agent, or Firm* — Hultquist, PLLC; Steven J. Hultquist

(57) ABSTRACT

The invention relates to an aqueous pharmaceutical composition comprising:
 a) bilastine or a pharmaceutically acceptable salt or solvate thereof,
 b) mometasone, or a pharmaceutically acceptable derivative thereof,
 c) a suspending agent, and
 d) 2-hydroxypropyl-β-cyclodextrin;
wherein the pH of the aqueous pharmaceutical composition is between 3.5 and 5.5, and wherein the content of 2-hydroxypropyl-β-cyclodextrin is less than 8.5% by weight.
The invention also relates to said compositions for use in the treatment and/or prevention of a disorder or disease susceptible to amelioration by antagonism of $H_1$ histamine receptor and/or of a corticosteroid-responsive disease through nasal administration.
The invention also relates to a process for preparing the aqueous pharmaceutical composition above mentioned.

19 Claims, 4 Drawing Sheets

Figure 1

AQUEOUS COMPOSITIONS COMPRISING BILASTINE AND MOMETASONE

CROSS-REFERENCE TO RELATED APPLICATIONS

This application is a U.S. national phase under the provisions of 35 U.S.C. § 371 of International Patent Application No. PCT/EP18/78034 filed Oct. 15, 2018, which in turn claims priority of European Patent Application No. EP17382686.8 filed Oct. 16, 2017. The disclosures of such international patent application and European priority patent application are hereby incorporated herein by reference in their respective entireties, for all purposes.

FIELD OF THE INVENTION

The present invention relates to aqueous pharmaceutical compositions of bilastine and a steroid, and to a method for preparing said aqueous pharmaceutical compositions. The present invention also relates to said compositions for use in the treatment and/or prevention of a disorder or disease susceptible to amelioration by antagonism of $H_1$ histamine receptor and/or of a corticosteroid-responsive disease, wherein said aqueous pharmaceutical composition is intranasally administered.

BACKGROUND

It has long been known that histamine plays a very important role in allergic-type diseases, such as allergic rhinitis, conjunctivitis, rhinoconjunctivitis, dermatitis, urticaria and asthma. Antihistaminic compounds acting at the $H_1$-receptor histamine level are useful for treating such conditions. In this sense, documents EP 0818454 A1 and EP 0580541 A1 as well as patent application EP14382576.8 disclose benzimidazole compounds with selective $H_1$ antihistaminic activity and devoid of arrhythmogenic effects.

A particular compound with the above properties is 2-[4-(2-{4-[1-(2-ethoxyethyl)-1H-benzimidazol-2-yl]-1-piperidinyl}ethyl)phenyl]-2-methylpropanoic acid, also known as bilastine, having formula:

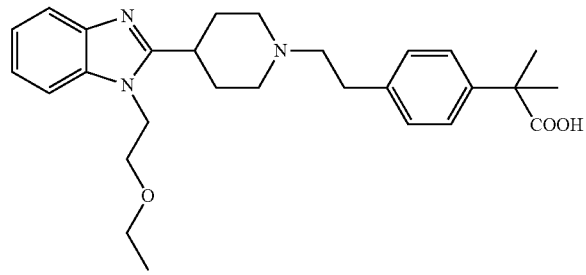 [SMILES: CCOCCn1c(C2CCN(CCc3ccc(C(C)(C)C(=O)O)cc3)CC2)nc2ccccc21]

and developed by Faes Farma, Spain. Bilastine is a $H_1$ antagonist benzimidazole compound with no sedative side effects, no cardiotoxic effects, and no hepatic metabolism. In addition, bilastine has proved to be effective for the symptomatic treatment of allergic rhinoconjunctivitis and urticaria.

On the other hand, steroids, particularly corticosteroids are believed to be helpful in alleviating respiratory disorders. In particular, glucocorticoids are believed to block many of the inflammatory pathways activated in respiratory disorders. Moreover, corticosteroids reduce or prevent inflammation of the airways contributing to the treatment of asthma symptoms, chronic obstructive pulmonary disease, or treating inflammation of the nasal passages in allergic conditions such as hay fever. The glucocorticoids for respiratory disorders such as asthma are preferably administered by inhalation to reduce the incidence of steroid-related side effects linked to systemic delivery.

A therapeutic composition has been recently reported in CN103784462 that combines the antihistaminic effect of bilastine with the anti-inflammatory effect of steroids for intranasal or eye drops. However, the low solubility of the bilastine in water impedes the proper administration of the disclosed pharmaceutical compositions via nasal.

KR 2013 0030606 A relates to pharmaceutical compositions comprising an antihistamine (which is not bilastine) and mometasone. US 2006/045850 A1 relates to the use of a cyclodextrin in improving the solubility of a steroid in an anti-inflammatory composition. EP 1 894 559 A1 addresses the problem of solubilizing poorly soluble corticoids for aerosol therapy by adding a cyclodextrin. US 2007/082870 A1 addresses the problem of increasing the aqueous solubility of an antifungal azole using cyclodextrins. These documents are silent regarding stable compositions comprising both bilastine and mometasone.

Therefore, there is a need in the art for a pharmaceutical composition with antihistaminic activities, which can also be used for treating corticosteroid-responsive diseases of the airway passage and/or lungs. Moreover, there is a need in the art of a pharmaceutical composition as above described that can be effectively administered via nasal.

BRIEF DESCRIPTION OF THE INVENTION

The present invention provides an aqueous pharmaceutical composition that combines the antihistaminic effect of benzimidazole derivatives with the treatment of corticosteroid-responsive diseases of the airway passage and/or lungs.

Thus, in a first aspect the invention relates to an aqueous pharmaceutical composition comprising:
  a) bilastine or a pharmaceutically acceptable salt or solvate thereof,
  b) mometasone or a pharmaceutically acceptable derivative thereof selected from an ester, ether and ketonide derivative,
  c) a suspending agent,
  d) 2-hydroxypropyl-β-cyclodextrin;
wherein the pH of the aqueous pharmaceutical composition is between 3.5 and 5.5, and wherein the content of 2-hydroxypropyl-p-cyclodextrin is less than 8.5% by weight.

The inventors of the present invention have surprisingly found that a content of less than 8.5% by weight of β-hydroxypropyl-p-cyclodextrin (HPBCD) in the aqueous pharmaceutical composition of the invention improves the solubility of benzimidazole derivatives, and solubilises a minimum quantity of the steroid mometasone or pharmaceutically acceptable derivative thereof, avoiding the degradation of the steroid mometasone, thereby maintaining the homogeneity and stability of the aqueous pharmaceutical composition.

In a second aspect the invention relates to a process for preparing an aqueous pharmaceutical composition comprising:
  a) preparing an aqueous solution of 2-hydroxypropyl-p-cyclodextrin, wherein the content of 2-hydroxypropyl-p-cyclodextrin is less than 8.5% by weight, b) adding bilastine, or a pharmaceutically acceptable salt or solvate thereof, to the aqueous solution of step a), and adding a buffer agent to obtain an aqueous solution of bilastine having a pH of between 3.5 and 5.5, c) preparing a dispersion of mometasone, or a pharmaceutically acceptable derivative thereof selected from an ester, ether and ketonide derivative with a surfactant in purified water, d) preparing an aqueous suspension of a suspending agent, e) adding the aqueous solution of step b) to the aqueous suspension of step d), and subsequently adding the dispersion of mometasone from step c) and homogenising the mixture under stirring, optionally adding a buffer to reach a pH of between 3.5 and 5.5.

In a third aspect the invention relates to an aqueous pharmaceutical composition as defined above for use as a medicament.

Another aspect of this invention refers to an aqueous pharmaceutical composition as defined above for use in the treatment and/or prevention of a disorder or disease susceptible to amelioration by antagonism of $H_1$ histamine receptor and/or of a corticosteroid-responsive disease.

In another aspect the invention relates to a nasal spray device comprising the aqueous pharmaceutical composition above described.

These aspects and preferred embodiments thereof are additionally also defined in the claims.

BRIEF DESCRIPTION OF THE FIGURES

FIG. 1 in graph A therein shows the change in the solubility of bilastine with the content of 2-hydroxypropyl-β-cyclodextrin in the range of pH of between 4.3 and 4.9.

FIG. 1 in graph B therein shows the change in the solubility of mometasone furoate with the content of 2-hydroxypropyl-β-cyclodextrin.

FIG. 3 in graph B therein shows the influence of kolliphor RH40 in the solubility of mometasone furoate monohydrate.

DETAILED DESCRIPTION OF THE INVENTION

Figure 2:
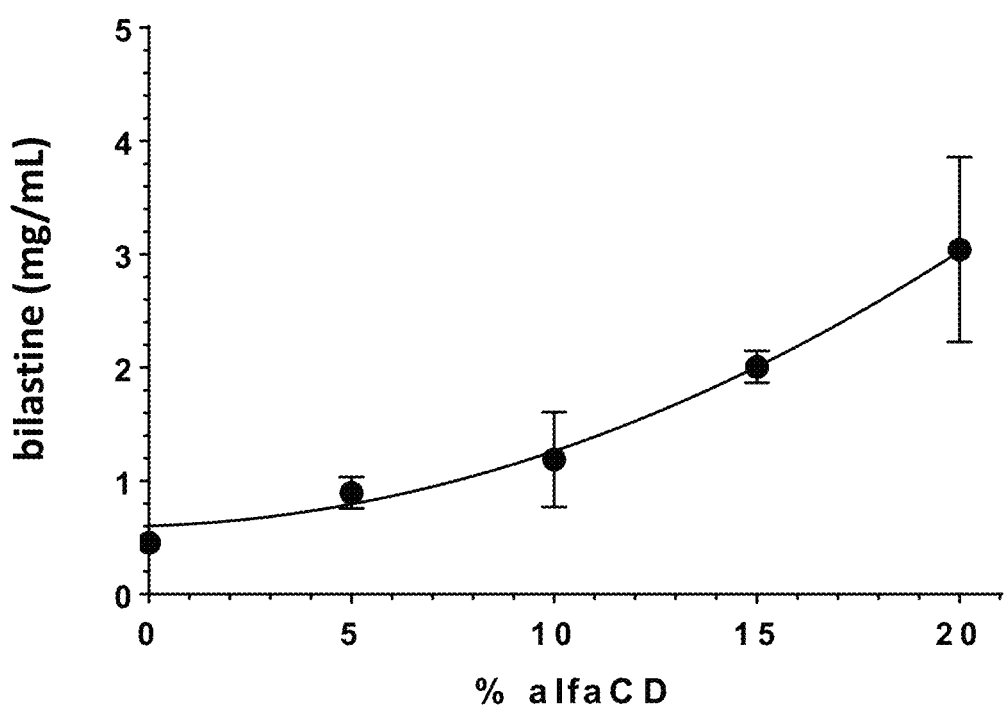
FIG. 2 shows the change in the solubility of bilastine with the content of α-cyclodextrin in a pH of 4.5.

The present invention provides an aqueous pharmaceutical composition containing benzimidazole derivatives and mometasone or a pharmaceutically acceptable derivative thereof. In particular, the combination of benzimidazole derivatives with mometasone or a pharmaceutically acceptable derivative thereof allows the treatment and/or prevention of disorders or diseases susceptible to amelioration by antagonism of $H_1$ histamine receptor, and of corticosteroid-responsive diseases though nasal administration. Besides, the stability and homogeneity of the aqueous pharmaceutical composition of the invention allows its effective administration by nasal spray.

In a first aspect, the invention relates to an aqueous pharmaceutical composition comprising:

a) bilastine or a pharmaceutically acceptable salt or solvate thereof b) mometasone or a pharmaceutically acceptable derivative thereof selected from an ester, ether and ketonide derivative, c) a suspending agent, d) 2-hydroxypropyl-β-cyclodextrin;

wherein the pH of the aqueous pharmaceutical composition is between 3.5 and 5.5, and wherein the content of 2-hydroxypropyl-β-cyclodextrin is less than 8.5% by weight.

"Pharmaceutical composition" as used herein, relates to compositions and molecular entities that are physiologically tolerable and do not typically produce an allergic reaction or a similar unfavorable reaction as gastric disorders, dizziness and suchlike, when administered to a human or animal. Preferably, the term "pharmaceutically acceptable" means it is approved by a regulatory agency of a state or federal government or is included in the U.S. Pharmacopoeia or other generally recognized pharmacopoeia for use in animals, and more particularly in humans.

The expression "aqueous pharmaceutical composition" refers to a liquid pharmaceutical composition comprising water. In the context of the present invention, the term "aqueous" means that said composition comprises water, preferable at least 1 wt % of water with respect to the total weight of the composition, more preferably at least 10 wt % of water, more preferably at least 20 wt % of water, more preferably at least 30 wt % of water, more preferably at least 40 wt % of water, more preferably at least 50 wt % of water, more preferably at least 60 wt % of water, more preferably at least 70 wt % of water, more preferably at least 80 wt % of water, more preferably at least 85 wt % of water, more preferably at least 90 wt % of water. In a particularly preferred embodiment, the aqueous pharmaceutical compositions of the present invention comprise at least 80 wt % of water with respect to the total weight of the composition.

In a particular embodiment, the aqueous pharmaceutical composition of the invention comprises between 0.2 and 0.8 wt. % of bilastine or a pharmaceutically acceptable salt or solvate thereof, between 1 and 8.5 wt. % of 2-hydroxypropyl-β-cyclodextrin, between 0.02 and 0.06 wt. % of mometasone or a pharmaceutically acceptable derivative thereof, between 1.0 and 2.5 wt. % of a suspending agent, based on the total weight of the composition.

In another particular embodiment, the aqueous pharmaceutical composition of the invention comprises between 0.2 and 0.8 wt. % of bilastine or a pharmaceutically acceptable salt or solvate thereof, between 1 and 5 wt. % of 2-hydroxypropyl-β-cyclodextrin, between 0.02 and 0.06 wt. % of mometasone or a pharmaceutically acceptable derivative thereof, between 1.0 and 2.5 wt. % of a suspending agent, based on the total weight of the composition.

The components of the aqueous pharmaceutical composition of the invention are further described below.

Bilastine

The aqueous pharmaceutical composition of the invention comprises a compound of formula:

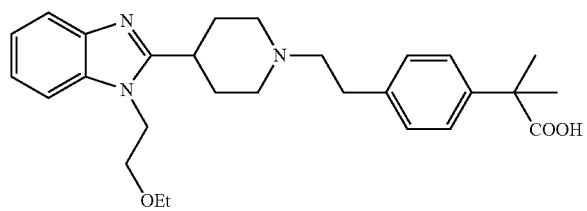 [SMILES: CCOCCn1c(C2CCN(CCc3ccc(C(C)(C)C(=O)O)cc3)CC2)nc2ccccc21]

or a pharmaceutically acceptable salt or solvate thereof. This compound is the 2-[4-(2-{4-[1-(2-ethoxyethyl)-1H-benzimidazol-2-yl]-1-piperidinyl}ethyl)phenyl]-2-methyl-propanoic acid, also known as bilastine. The synthesis of bilastine has been described in documents EP 0818454 A1 and EP 0580541 A1, and the patent application EP14382576.8.

Bilastine may be in the form of salts or solvates, preferably pharmaceutically acceptable salts or solvates.

The term "pharmaceutically acceptable salts" as used herein encompasses any salt with no limitation on the type of salt that can be used, provided that these are acceptable for administration to a patient, meaning that they do not induce undue toxicity, irritation, allergic responses, or the like. Pharmaceutically acceptable salts are well known in the art. By way of illustration, pharmaceutically acceptable salts of bilastine can be acid addition salts, base addition salts or metal salts, and can be synthesized from the parent compounds containing a basic or acid moiety by means of conventional chemical processes known by the persons skilled in the art. Such salts are generally prepared, for example, by reacting the free acid or base forms of said compounds with a stoichiometric amount of the suitable base or acid in water or in an organic solvent or in a mixture of the two. Non-aqueous media such as ether, ethyl acetate, ethanol, acetone, isopropanol or acetonitrile are generally preferred. Illustrative examples of acid addition salts include inorganic acid addition salts such as, for example, hydrochloride, hydrobromide, hydroiodide, sulfate, nitrate, phosphate, etc., organic acid addition salts such as, for example, acetate, maleate, fumarate, citrate, oxalate, succinate, tartrate, malate, mandelate, methanesulfonate, p-toluenesulfonate, camphorsulfonate, etc. Illustrative examples of base addition salts include inorganic base salts such as, for example, ammonium salts and organic base salts such as, for example, ethylenediamine, ethanolamine, N,N-dialkylenethanolamine, triethanolamine, glutamine, amino acid basic salts, etc. Illustrative examples of metal salts include, for example, sodium, potassium, calcium, magnesium, aluminum and lithium salts.

The term "solvate" according to this invention is to be understood as meaning any form of the active compound according to the invention which has another molecule (most likely a polar solvent) attached to it via non-covalent bonding. Examples of solvates include hydrates and alcoholates. Solvation methods are generally known in the state of the art.

The bilastine in the aqueous pharmaceutical composition of the invention is also meant to include compounds which differ only in the presence of one or more isotopically enriched atoms. For example, compounds having the present structures except for the replacement of an hydrogen by a deuterium or tritium, or the replacement of a carbon by a $^{13}C$— or $^{14}C$— enriched carbon or a nitrogen by $^{15}N$-enriched nitrogen are within the scope of this invention.

In a preferred embodiment, the amount of bilastine in the aqueous pharmaceutical composition of the invention is comprised between 0.2 and 0.8 wt. %, based on the total weight of the composition. Preferably, the amount of bilastine in the aqueous pharmaceutical composition of the present invention is comprised between 0.3 and 0.7 wt. %, more preferably between 0.4 and 0.6 wt. %. In a more preferred embodiment, the amount of bilastine in the aqueous pharmaceutical composition of the invention is 0.4 wt. %.

Mometasone

The aqueous pharmaceutical composition of the invention contains mometasone and/or a pharmaceutically acceptable derivative thereof. Generally, steroids, such as mometasone, possess regulatory functions in cells, tissues and organisms.

The term "pharmaceutically acceptable derivatives thereof" refers to non-toxic functional equivalents or derivatives of mometasone, which can be obtained by substitution of atoms or molecular groups or bonds of mometasone, whereby the basic structure is not changed, and which differ from the structure of mometasone in at least one position. Particularly, pharmaceutically acceptable derivatives of mometasone in the context of the present invention refer to an ester, ether or ketonide of mometasone. That is, to compounds wherein at least one of the hydroxyl groups of mometasone is functionalized as an ester, ether or ketonide. Thus, in a particular embodiment the aqueous pharmaceutical composition of the invention comprises a pharmaceutically acceptable derivative of mometasone selected from ester, ether and ketonide.

In a particular embodiment, an ester derivative of mometasone refers to mometasone wherein at least one —OH group is replaced by a —OC(O)R' group, wherein R' is selected from $C_1$-$C_6$ alkyl, halo($C_1$-$C_6$ alkyl), ($C_6$-$C_{12}$)aryl ($C_1$-$C_6$)alkyl, $C_3$-$C_7$ cycloalkyl, 3- to 10-membered heterocyclyl, $C_6$-$C_{12}$ aryl, and 3- to 10-membered heteroaryl. In a particular embodiment, R' is selected from $C_1$-$C_6$ alkyl, and 3- to 10-membered heteroaryl, such as methyl, ethyl, propyl, butyl, furyl, thiophenyl or pyridinyl. In a particular embodiment, the ester derivative is a furoate or a propionate, such as mometasone furoate and mometasone propionate. In a preferred embodiment, the aqueous pharmaceutical composition of the present invention contains mometasone furoate.

In a particular embodiment, an ether derivative of mometasone refers to mometasone wherein at least one —OH group is replaced by a —OR' group, wherein R' is selected from $C_1$-$C_6$ alkyl, halo($C_1$-$C_6$ alkyl), ($C_6$-$C_{12}$)aryl($C_1$-$C_6$) alkyl, $C_3$-$C_7$ cycloalkyl, 3- to 10-membered heterocyclyl, $C_6$-$C_{12}$ aryl, and 3- to 10-membered heteroaryl.

In a particular embodiment, a ketonide derivative of mometasone refers to mometasone wherein two —OH groups disposed either on contiguous carbons or on two carbons having one carbon disposed between them, taken together form a group of formula

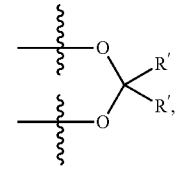

wherein each R' is independently selected from $C_1$-$C_6$ alkyl, halo($C_1$-$C_6$ alkyl), ($C_6$-$C_{12}$)aryl($C_1$-$C_6$)alkyl, $C_3$-$C_7$ cycloalkyl, 3- to 10-membered heterocyclyl, $C_6$-$C_{12}$ aryl, and 3- to 10-membered heteroaryl. In a particular embodiment, each R' is independently selected from $C_1$-$C_6$ alkyl, such as methyl, ethyl, propyl or butyl. In a particular embodiment, the ketonide derivative is an acetonide, i.e. R' is methyl, such as triamcinolone acetonide.

Methods for the preparation of these mometasone derivatives are well-known in the art (e.g. e.g. M. B. Smith, J. March, March's Advanced Organic Chemistry, Wiley-Interscience, 5$^{th}$ ed.). Likewise, the mometasone and mometasone derivatives may be present in the aqueous pharmaceutical composition both as free compounds or as solvates (e.g., hydrates, alcoholates, etc.), both forms being included within the scope of the present invention. Thus, for example, suitable forms of mometasone furoate in the aqueous pharmaceutical composition of the invention include anhydrous form or hydrate form, such as monohydrate form. In a preferred embodiment, the aqueous pharmaceutical composition of the invention contains mometasone hydrate. The solvation methods are well known in the state of the art.

In a preferred embodiment, the amount of mometasone or a pharmaceutically acceptable derivative thereof in the aqueous pharmaceutical composition of the invention is comprised between 0.02 and 0.06 wt. % based on the total weight of the composition, preferably 0.05 wt. %.

Suspending Agent

The term "suspending agent" refers to an agent that overcomes agglomeration of dispersed particles in a liquid medium, and increases the viscosity of the medium so that the particles settle more slowly (Remington, *The Science and practice of pharmacy*, 21 st edition, p. 1072, 2005).

In a particular embodiment, the suspending agent in the aqueous pharmaceutical composition of the invention is selected from cellulose and/or cellulose derivatives wherein the hydroxyl groups of cellulose have been partially or fully substituted to provide cellulose ethers (—OR). In a preferred embodiment, the suspending agent in the aqueous pharmaceutical composition of the invention is a cellulose ether derivative selected from microcrystalline cellulose (MCC), methyl cellulose, carboxymethyl cellulose, sodium carboxymethylcellulose (Na-CMC), hydroxypropyl-methyl cellulose (HPMC) or mixtures thereof. Suspending agents suitable for the pharmaceutical composition of the present invention are commercially available under the trade name Vivapur® MCG (JRS Pharma), Avicel® RC591 (FMC Biopolymer) and Avicel® RC581 (JRS Pharma).

Particularly, when the aqueous pharmaceutical composition of the invention is applied in nasal delivery devices, Avicel RC591 and Vivapur MCG are preferably used due to its thixotropic properties. Both compounds form a gel network that keeps drug particles suspended in nasal delivery devices. During agitation and pumping, the gel becomes fluid and enables an eased spraying that results in an efficient, standardized and optimum atomization and deposition pattern. After agitation, the fluid regains its viscosity preventing the dripping from the nose or outflow into the throat area, prolonging the retention time of the drug substance in the nasal cavity. Preferably, Avicel RC-591 is used at 20 mg/ml (2.0 wt. %), while a concentration of 18 mg/ml (1.8 wt. %) of Vivapur MCG 811P is recommended in the aqueous pharmaceutical composition of the invention.

The aqueous pharmaceutical composition of the present invention contains between 1.0 and 2.5 wt. % of the suspending agent based on the total weight of the composition, preferably between 1.3 and 2 wt. %, even more preferably between 1.6 and 1.9 wt. %, even more preferably 1.8 wt. %. The inventors have found that a content lower than 1 wt. % produces too fluid dispersions, while a content over this value produces thixotropic gels.

2-hydroxypropyl-β-cyclodextrin The aqueous pharmaceutical composition of the present invention also comprises 2-hydroxypropyl-β-cyclodextrin (HPBCD) wherein the content of said cyclodextrin is less than 8.5% by weight.

As described throughout the text, and unless stated otherwise, a content of less than 8.5% by weight is to be understood as a content of less than 85 mg/mL of formulation.

In a particular embodiment, the aqueous pharmaceutical composition of the present invention contains between 1 and 8.5% wt. of HPBCD. In another particular embodiment, the aqueous pharmaceutical composition of the present invention contains between 2 and 8.5% wt. of HPBCD.

In yet another particular embodiment, the aqueous pharmaceutical composition of the present invention contains less than 5% wt. of HPBCD.

In a particular embodiment the aqueous pharmaceutical composition of the present invention contains between 1 and 5% wt. of HPBCD. In a preferred embodiment the content of HPBCD is comprised between 2 and 4% wt., more preferably the content of HPBCD is 3% wt.

Bilastine is slightly soluble in water, and its solubility depends on the pH, becoming more hydrophilic at pH<3.6 and pH>8.5 and more hydrophobic at pH in the range of 3.8-8.5. Therefore, in the range of pH of the aqueous pharmaceutical composition of the invention of between 3.5 and 5.5, a solubiliser of bilastine is required.

Figure 1:
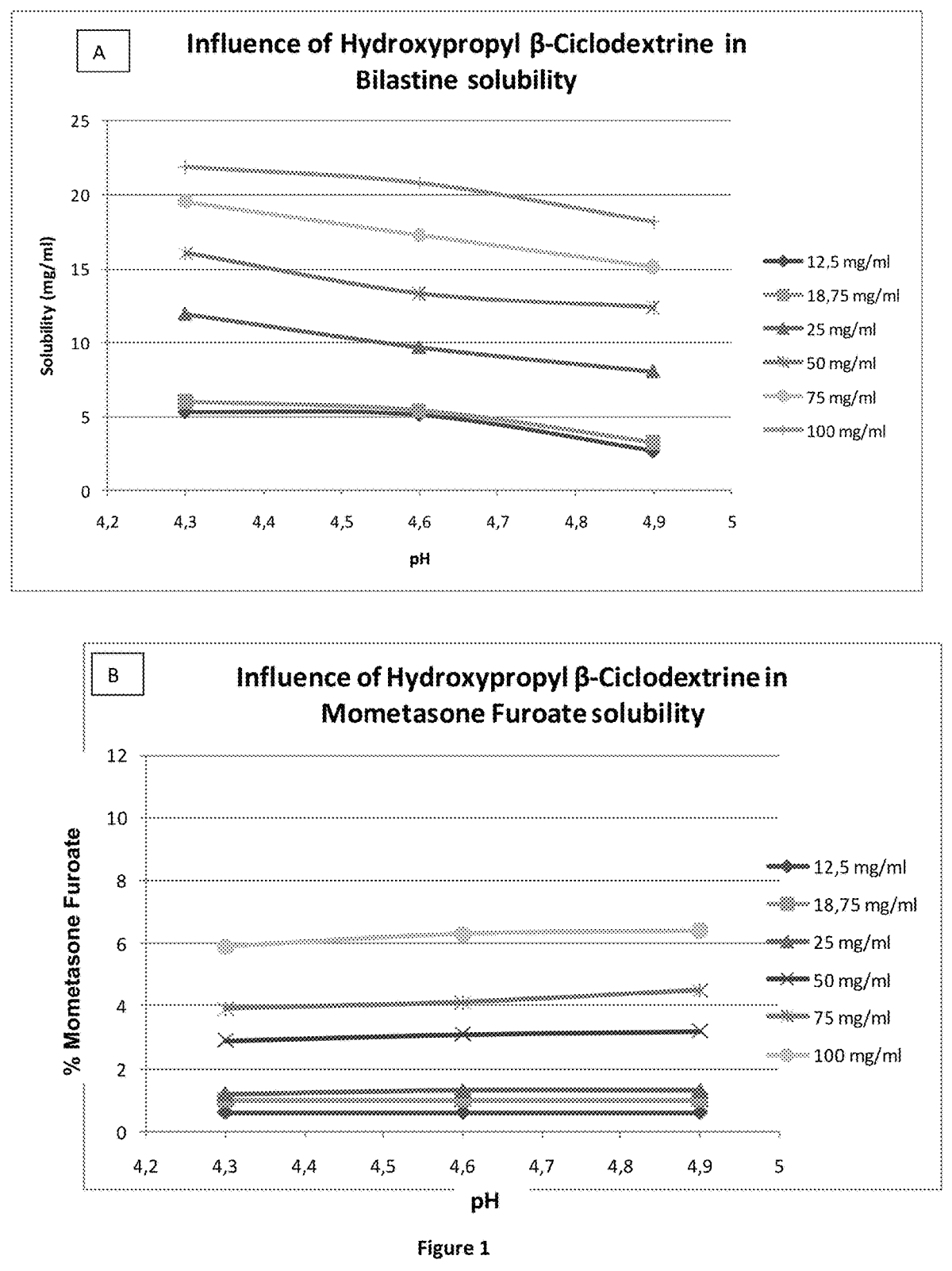

The inventors have surprisingly found that that there is a direct linear relationship between the percentage of solubilized mometasone and the percentage of the resulting impurities. In addition, the inventors found that the presence of HPBCD cyclodextrin in the present pharmaceutical composition allows the provision of a formulation comprising bilastine and mometasone which is stable in the sense that it minimizes the degradation of the steroid below pharmaceutical acceptable levels while it ensures that the proper amount of bilastine is solubilised. In this sense, while HPBCD produces the solubilisation of bilastine in the range of pH of the aqueous pharmaceutical composition of the invention, other cyclodextrines, such as α-cyclodextrine (α-CD), do not lead to the required solubility. FIG. 1 in graph A therein shows the change of the solubility of bilastine with the content of hydroxypropyl-β-cyclodextrin in a pH range of between 4.3 and 4.9. In particular, FIG. 1 in graph A therein shows that for a content of 25 mg/ml of hydroxypropyl-β-cyclodextrin (2.5 wt. %) the solubility of bilastine is around 10 mg/ml at a pH value of 4.6. By contrast, when 5 wt. % of α-cyclodextrine (α-CD) is used instead of HPBCD, the solubility of bilastine does not reach 1 mg/ml, as FIG. 2 shows at a pH of 4.5.

Moreover, FIG. 1 in graph B therein shows that the solubility of mometasone furoate remains around 4 mg/ml when the content of HPBCD is 75 mg/ml (7.5 wt. %). In this sense, the inventors have also found that a content of HPBCD of less than 8.5% by weight in the aqueous pharmaceutical composition of the invention, produces the complete dissolution of bilastine while, at the same time, a minimum quantity of mometasone is dissolved, thereby minimizing the unwanted degradation of the steroid below pharmaceutical acceptable levels.

In addition, HPBCD in the pharmaceutical composition of the invention also masks the unpleasant flavours of the composition, favouring the administration of the pharmaceutical composition to the patient.

In the context of the present invention HPBCD may have different degrees of substitution. For example, Cavasol W7 HP™ and Cavasol W7 HP5™ (Ashland) having a degree of substitution of between 4.1 and 5.1, Cavitron W7 HP7™ (Ashland), Kleptose HPB™ (Roquette's) having a degree of substitution of 4.5, Kleptose HP™ (Roquette's) having a degree of substitution of 5.6 (HP8BCD) and Trappsol having a degree of substitution of 3.5 and 6.5 (CTD) are commercially available.

pH

The pH of the aqueous pharmaceutical composition of the invention is between 3.5 and 5.5.

In a particular embodiment, the pH of the aqueous pharmaceutical composition of the invention is comprised between 4.0 and 5.0. In another particular embodiment the pH of the aqueous pharmaceutical composition is between 4.3 and 4.9 In a preferred embodiment the pH of the aqueous pharmaceutical composition of the invention is 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4 or 5.5. Preferably, the pH of the aqueous pharmaceutical composition of the invention is 4.0, 4.1, 4.2, 4.3, 4.4, 4.5, 4.6, 4.7, 4.8, 4.9 or 5.0. More preferably, the pH of the aqueous pharmaceutical composition of the invention is 4.3, 4.4, 4.5, 4.6, 4.7, 4.8 or 4.9.

The aqueous pharmaceutical composition of the invention has been developed for nasal administration. The physiological pH of the nasal cavity, particularly of the human nasal cavity, is between about 5.5-6.5, and increases in rhinitis to about 7.2-8.3.

In a preferred embodiment, the aqueous pharmaceutical composition further comprises a buffer agent. As used herein, the term "buffer agent" refers to an agent that imparts suitable pH characteristics to the aqueous pharmaceutical composition provided herein. Said buffer agents are used for adjusting the pH of the compositions of the invention to a pH of from 3.5 to 5.5, more preferably to a pH of from 4.0 to 5.0, even more preferably to a pH of between 4.3 to 4.9, even more preferably 4.6.

The pH values mentioned in the present application have been measured at room temperature with a pHmeter, particularly by direct reading from pHmeter Crison Microph 2000. In the context of the present invention, the pH of the pharmaceutical composition of the invention may be measured by any other device suitable for measuring the pH in the composition.

In a particular embodiment, the aqueous pharmaceutical composition of the invention comprises a buffering agent selected from acetate buffer, citrate buffer, phosphate buffer, borate buffer, or a combination thereof. In a preferred embodiment, the buffer agent is selected from sodium citrate hemihydrates, citric acid anhydrous and mixtures thereof. More preferably, the buffer agent is selected from citric acid monohydrate and trisodium citrate dihydrate.

In a particular embodiment, the aqueous pharmaceutical composition contains between 0.15 and 0.20 wt. % of a buffer agent. In a preferred embodiment, the aqueous pharmaceutical composition contains between 0.17 and 0.19 wt. % of a buffer agent. More preferably, the aqueous pharmaceutical composition of the invention contains 2.0 mg/ml of citric acid monohydrate.

The pH range of the aqueous pharmaceutical composition of the invention maintains the chemical, physical, and/or physiological stability of the aqueous pharmaceutical composition and is well-tolerated by the nasal cavities.

Additional Excipients

The aqueous pharmaceutical composition of the invention may further comprise additional excipients. In a particular embodiment the aqueous pharmaceutical composition of the invention comprises a humectant, a surfactant, a preservative, a tonicity agent, and/or combinations thereof.

Preferably, the aqueous pharmaceutical composition comprises between 0.005% and 0.03 wt. % of a surfactant, between 1 and 3 wt. % of a humectant, between 0.010 and 0.026 wt. 30% of a preservative.

In another particular embodiment, the aqueous pharmaceutical composition of the invention further comprises a humectant selected from anhydrous glycerine, glycerol and propylene glycol. Preferably, the humectant in the aqueous pharmaceutical composition of the invention is anhydrous glycerine.

In another particular embodiment, the aqueous pharmaceutical composition of the invention contains a surfactant agent. It is believed that the surfactant agent may lower the surface tension of the composition, easing the manufacturing process. Examples of suitable surfactant agents may be selected from, but not limited to polyethoxylated sorbitan derivatives such as polysorbates, their ether ethoxylates, produced by reaction of sorbitan esters with ethylene oxide, polyoxyethylene alkyl phenol, polyoxyethylene cetyl ether, polyoxyethylene alkyl-aryl ether, polyoxyethylene monolaurate, polyoxyethylene vegetable oil, polyoxyethylene sorbitan monolaurate, polyoxyethylene esters or mixed fatty and resin acids, polyoxyethylene sorbitol lanolin derivative, polyoxyethylene tridecylether, polyoxyethylene sorbitan esters of mixed fatty and resin acids, polyethoxylated sorbitan derivatives or esters of fatty acids (e.g. Polysorbates), polyoxyethylene sorbitan monostearate, polyoxyethylene sorbitan monooleate, polyoxyethylene monostearate, polyoxyethylene stearyl ether, polyoxyethylene oleyl ether, polyoxyethylene tridecyl ether, polyoxyethylene fatty alcohol, polyoxyethylene alkyl amine, polyoxyethylene glycol monopalmitate, polyoxyethylene sorbitan monopalmitate, polyoxyethylene cetyl ether, polyoxyethylene oxypropylene stearate, polyoxyethylene lauryl ether, polyoxyethylene lanolin derivative, sodium oleate, quaternary ammonium derivative, potassium oleate, N-cetyl N-ethyl morpholinium ethosulfate, sodium lauryl sulfate or mixtures thereof. Particularly preferred surfactants are Polysorbate 80, Polysorbate 40, Polysorbate 60, sorbitan monolaurate, sorbitan monopalmitate, sorbitan monostearate, polyoxyl 40 hydrogenated castor oil (Cremophor RH 40), polyoxyethylene alkyl ether (—BO-10V, Cremophor A20, Cremophor A25), poloxamers, phospholipids and propylene glycol. In a preferred embodiment, the aqueous pharmaceutical composition of the invention comprises between 0.005 and 0.03 wt. % of surfactant. Preferably, the aqueous pharmaceutical composition of the invention comprises Polysorbate 80 as surfactant agent. Polysorbate 80 may lower the surface tension of the composition, easing the manufacturing process. In a preferred embodiment, the aqueous pharmaceutical composition of the invention comprises between 0.005 and 0.03 wt. % of Polysorbate 80.

In another particular embodiment, the aqueous pharmaceutical composition of the invention further comprises a preservative selected from benzalkonium chloride, sodium benzoate, phenylethyl alcohol, chlorobutanol, parabens, EDTA and benzoyl alcohol and phenoxyethanol.

In another particular embodiment, the aqueous pharmaceutical composition comprises a tonicity agent. In particular, when the aqueous pharmaceutical composition of the invention is used as nasal spray suspension, the tonicity agent may help to maintain the osmolarity of the aqueous pharmaceutical composition as close as possible to the physiological values. In a preferred embodiment the tonicity agent in the aqueous pharmaceutical composition of the invention is anhydrous glycerine, sorbitol, mannitol or propylene glycol. In a more preferred embodiment the tonicity agent is anhydrous glycerine. More preferably, the aqueous pharmaceutical composition of the invention contains 21 mg/ml (2.1 wt. %) of anhydrous glycerine.

Process for Preparing the Aqueous Pharmaceutical Composition of the Invention

In one aspect the invention relates to the process for preparing the aqueous pharmaceutical composition of the invention. The process of the invention comprises:
a) preparing an aqueous solution of 2-hydroxypropyl-β-cyclodextrin, wherein the content of 2-hydroxypropyl-β-cyclodextrin is less than 8.5% by weight,
b) adding bilastine or a pharmaceutically acceptable salt or solvate thereof, to the aqueous solution of step a), and adding a buffer agent to obtain an aqueous solution of bilastine having a pH of between 3.5 and 5.5,
c) preparing a dispersion of mometasone, or a pharmaceutically acceptable derivative thereof with a surfactant in purified water,
d) preparing an aqueous suspension of a suspending agent,
e) adding the aqueous solution of step b) to the aqueous suspension of step d), and subsequently adding the dispersion of mometasone from step c), and homogenising the mixture, optionally adding a buffer to reach a pH of between 3.5 and 5.5.

According to step a) of the process of the invention, an aqueous solution of 2-hydroxypropyl-β-cyclodextrin is prepared containing less than 8.5% by weight of 2-hydroxypropyl-β-cyclodextrin.

The inventors have found that a content of HPBCD of less than 8.5% by weight in the aqueous pharmaceutical composition of the invention produces the complete dissolution of bilastine while, at the same time, a minimum quantity of mometasone is dissolved, thereby preventing the unwanted degradation of the steroid below pharmaceutical acceptable levels.

In a particular embodiment, the aqueous solution of 2-hydroxypropyl-β-cyclodextrin contains between 1 and 8.5% wt. of HPBCD. In another particular embodiment, the aqueous solution of 2-hydroxypropyl-β-cyclodextrin contains between 2 and 8.5% wt. of HPBCD.

In yet another particular embodiment, the aqueous solution of 2-hydroxypropyl-β-cyclodextrin contains less than 5% wt. of HPBCD.

In a particular embodiment the aqueous solution of 2-hydroxypropyl-β-cyclodextrin contains between 1 and 5 wt. % of HPBCD, preferably contains between 2 and 4% wt. of HPBCD. In a preferred embodiment the content of HPBCD is 3% by weight.

Suitable HPBCD in the context of the present invention include HPBCD having different degrees of substitution. For example, Cavasol W7 HP™ and Cavasol W7 HP5™ (Ashland) having a degree of substitution of between 4.1 and 5.1, Cavitron W7 HP7™ (Ashland), Kleptose HPB™ (Roquette's) having a degree of substitution of 4.5, Kleptose HP™ (Roquette's) having a degree of substitution of 5.6 (HP8BCD) and Trappsol having a degree of substitution of 3.5 and 6.5 (CTD) are commercially available.

In a preferred embodiment a buffer agent is added to the aqueous solution of HPBCD to reach a pH of between 3.5 and 5.5, preferably between 4 and 5, more preferably between 4.3 and 4.9, even more preferably between 4.4 and 4.6, even more preferably 4.45. Preferably, the buffer agent is selected from citric acid monohydrate or trisodium citrate dihydrate.

According to step b) bilastine or a pharmaceutically acceptable salt or solvate thereof is added to the aqueous solution of step a), and a buffer agent is added to obtain an aqueous solution having a pH of between 3.5 and 5.5.

In a preferred embodiment the buffer agent is added to obtain an aqueous solution having a pH of between 4 and 5, more preferably between 4.3 and 4.9, even more preferably between 4.4 and 4.6, even more preferably 4.45. The pH values mentioned in the present application have been measured with a pHmeter, particularly by direct reading from pHmeter Crison Microph 2000. The buffer agent is preferably added to the aqueous solution under stirring conditions. In a preferred embodiment, the buffer agent is selected from citric acid monohydrate or trisodium citrate dihydrate.

The inventors have found that the presence of bilastine or a pharmaceutically acceptable salt or solvate thereof increases the pH of the aqueous solution, thereby a buffer agent is usually necessary to maintain the pH between 3.5 and 5.5.

In one particular embodiment, a buffer agent is added to the aqueous solution in steps a) and/or b).

In a preferred embodiment, the amount bilastine in the aqueous pharmaceutical composition of the invention is comprised between 0.2 and 0.8 wt. %, based on the total weight of the composition. Preferably, the amount of bilastine in the aqueous pharmaceutical composition of the present invention is comprised between 0.3 and 0.7 wt. %, more preferably between 0.4 and 0.6 wt. %. In a more preferred embodiment, the aqueous pharmaceutical composition of the invention is 0.4 wt. %.

Moreover, optionally, a preservative can be added to the aqueous solution under stirring conditions. In one particular embodiment, a preservative is added to the aqueous solution once bilastine is dissolved in step b).

According to step c), a dispersion is formed by dispersing mometasone or a pharmaceutically acceptable derivative thereof with a surfactant in purified water. Surfactants lower the surface tension of the dispersion increasing the homogeneity and stability. Moreover, the surfactant eases the wetting and dispersion of mometasone or a pharmaceutically acceptable derivative thereof in water, thereby facilitating the manufacturing process. Suitable surfactants in this step include Polysorbate 80. In a preferred embodiment a dispersion is formed by dispersing mometasone or a pharmaceutically acceptable derivative thereof together with between 0.005 and 0.03 wt. % of Polysorbate 80.

The mometasone and mometasone derivatives to be dispersed in step c) may be in free form or as solvates (e.g., hydrates, alcoholates, etc.), both forms being included within the scope of the present invention. The solvation methods are generally known in the state of the art. Preferably, the solvate is a hydrate.

In a preferred embodiment, a dispersion is formed by dispersing mometasone furoate with a surfactant in purified water. More preferably, mometasone furoate is in anhydrous form or in a hydrate form, such as monohydrate form.

In a particular embodiment, the amount of mometasone or a pharmaceutically acceptable derivative in the dispersion is comprised between 0.02 and 0.06 wt. % based on the total weight of the composition, preferably 0.05 wt. %.

According to step d) of the process of the invention, an aqueous suspension of a suspending agent is prepared. In a particular embodiment the suspending agent is selected from cellulose, cellulose derivatives and mixtures thereof. Preferably, the suspending agent in the aqueous suspension is selected from microcrystalline cellulose (MCC), methyl cellulose, carboxymethyl cellulose, sodium carboxymethyl-cellulose (Na-CMC), hydroxypropyl-methyl cellulose (HPMC) and mixtures thereof. More preferably, the suspending agent in the aqueous suspension is selected from microcrystalline cellulose (MCC) or sodium carboxymethylcellulose (Na-CMC). The preferred suspending agents are commercially available under the tradenames Vivapur® MCG (JRS Pharma), Avicel® RC591 (FMC Biopolymer) and Avicel® RC581 (JRS Pharma).

The aqueous suspension of a suspending agent in step d) may contain between 1.0 and 2.5 wt. % of the suspending agent based on the total weight of the composition, preferably between 1.3 and 2 wt. %, even more preferably between 1.6 and 1.8 wt. %.

The aqueous suspension of step d) can be prepared by dissolving the suspending agent in deionized water under stirring conditions. The aqueous suspension can be further homogenized by stirring. Preferably, the aqueous suspension is homogenized by stirring to obtain a suspension phase. The homogeneity assessment is carried out by observing the sample to detect the absence of phase separation or agglomerates.

Particularly, microcrystalline cellulose (MCC) and/or sodium carboxymethylcellulose (Na-CMC) requires an activation step to work as suspending agent in the aqueous pharmaceutical composition of the invention. In a particular embodiment, the suspending agent selected from microcrystalline cellulose (MCC), sodium carboxymethylcellulose (Na-CMC) and mixtures thereof are activated by dispersion in water and applying high shear forces. The high shear forces broke up the particles and allow the formation of the gel network.

In a preferred embodiment the suspending agent is activated by firstly preparing an aqueous solution of the suspending agent containing a volume of water comprised between 30% and 40% with respect to the total volume, preferably between 33% and 37%, even more preferably between 34% and 36% volume of water, even more preferably 35% volume of water. The suspending agent is added to water under stirring. The resulting aqueous suspension is homogenised by applying high shear forces. The homogeneity assessment is carried out by observing the sample to detect the absence of phase separation or agglomerates.

In a preferred embodiment, in step d) an aqueous suspension of a suspending agent further containing a tonicity agent is prepared. Particularly, when the aqueous pharmaceutical composition of the invention is used as nasal spray suspension, the tonicity agent helps to maintain the osmolarity of the aqueous pharmaceutical composition as close as possible to the physiological values. Preferably, the tonicity agent in the aqueous pharmaceutical composition of the invention is anhydrous glycerine or glycerol, more preferably anhydrous glycerine. More preferably, the aqueous pharmaceutical composition of the invention contains 21 mg/ml (2.1 wt. %) of anhydrous glycerine.

Moreover, optionally, humectants can be added to the aqueous suspension of the suspending agent under stirring conditions. In one particular embodiment, in step d) an aqueous suspension of a suspending agent further containing a humectant is prepared. In another preferred embodiment, in step d) an aqueous suspension of a suspending agent, further containing a humectant, and a tonicity agent is prepared.

In step e) of the process of the invention the aqueous solution of step b) is added to the aqueous suspension of step d), and subsequently the dispersion of mometasone from step c) is also added. The resulting mixture is homogenised by stirring.

Optionally, a buffer agent can be added to the homogenized mixture containing the steroid to obtain the final formulation with a pH of between 3.5 and 5.5. In one preferred embodiment, the pH of the final formulation is of between 4.0 and 5.0, more preferably of between 4.3 and 4.9. In a more preferred embodiment the pH of the final formulation is about 4.6. Suitable buffering agents include acetate buffer, a citrate buffer, a phosphate buffer, a borate buffer, or a combination thereof. Preferably, the buffer agent is selected from sodium citrate hemihydrates, citric acid anhydrous and mixtures thereof.

Uses

Bilastine has been found to be an antagonist of histamine $H_1$ receptor and would thus be useful in the treatment and/or prevention of diseases known to be susceptible to improvement by antagonism of histamine $H_1$ receptor. The skilled person readily identifies which diseases are known to be susceptible to improvement by antagonism of histamine $H_1$ receptor. As an example, such diseases are allergic rhinitis, allergic conjunctivitis, urticaria, CNS diseases (Simons, F. Estelle R., and Keith J. Simons. "Histamine and H1-antihistamines: celebrating a century of progress." *Journal of Allergy and Clinical Immunology* 128.6 (2011): 1139-1150) or redness, itching and swelling, rhinorrhea, bronchoconstriction, anaphylaxis, urticaria as well as regulation of food intake and sleep, convulsion, and attention (Kalpaklioglu, Fusun, and Ayse Baccioglu. "Efficacy and safety of H1-antihistamines: an update." Anti-Inflammatory & Anti-Allergy Agents in Medicinal Chemistry (Formerly Current Medicinal Chemistry-Anti-Inflammatory and Anti-Allergy Agents) 11.3 (2012): 230-237).

Moreover, mometasone or pharmaceutically acceptable derivatives thereof in the aqueous pharmaceutical composition of the invention reduces or prevents inflammation of the airways passages contributing to alleviate respiratory disorders.

Therefore, an aspect of the invention refers to the aqueous pharmaceutical composition of the invention for use as a medicament.

Another aspect of the invention refers to an aqueous pharmaceutical composition of the invention for use in the treatment and/or prevention of a disorder or disease susceptible to amelioration by antagonism of $H_1$ histamine receptor and/or of a corticosteroid-responsive disease. A preferred embodiment refers to the aqueous pharmaceutical composition of the invention for use in the treatment and/or prevention of a disorder or disease susceptible to amelioration by antagonism of $H_1$ histamine receptor and/or of a corticosteroid-responsive disease, wherein said aqueous pharmaceutical composition is intranasally administered.

The invention also refers to the method for the treatment and/or prevention of a disorder or disease susceptible to amelioration by antagonism of $H_1$ histamine receptor and/or a corticosteroid-responsive disease comprising administering an effective amount of an aqueous pharmaceutical composition of the invention. A preferred embodiment refers to the method for the treatment and/or prevention of a disorder or disease susceptible to amelioration by antagonism of $H_1$ histamine receptor and/or a corticosteroid-responsive disease comprising administering an effective amount of an aqueous pharmaceutical composition of the invention, wherein said aqueous pharmaceutical composition is intranasally administered.

The invention also refers to the use of the aqueous pharmaceutical composition of the invention for the manufacture of a medicament for the treatment and/or prevention of a disorder or disease susceptible to amelioration by antagonism of $H_1$ histamine receptor and/or a corticosteroid-responsive disease. A preferred embodiment, refers to the use of the aqueous pharmaceutical composition of the invention for the manufacture of a medicament for the treatment and/or prevention of a disorder or disease susceptible to amelioration by antagonism of $H_1$ histamine receptor and/or a corticosteroid-responsive disease, wherein said aqueous pharmaceutical composition is intranasally administered.

The invention provides an aqueous pharmaceutical composition for use in the treatment and/or prevention of a disorder or disease susceptible to amelioration by antagonism of $H_1$ histamine receptor. Thus, in a particular embodiment the invention relates to an aqueous pharmaceutical composition for use in the treatment and/or prevention of a disorder or disease susceptible to amelioration by antagonism of $H_1$ histamine receptor wherein said disorder or disease is selected from rhinitis, conjunctivitis and rhinoconjunctivitis. Preferably, the aqueous pharmaceutical composition is intranasally administered.

The invention also provides an aqueous pharmaceutical composition for use in the treatment of a corticosteroid-responsive disease. In a particular embodiment, the invention also provides an aqueous pharmaceutical composition for use in the treatment of a corticosteroid-responsive disease selected from asthma, allergic and non-allergic rhinitis, non-malignant proliferative and inflammatory diseases. Preferably, the aqueous pharmaceutical composition is intranasally administered.

The term "treatment" or "to treat" in the context of this specification means administration of the aqueous pharmaceutical composition according to the invention to ameliorate or eliminate the disease or one or more symptoms associated with said disease. "Treatment" also encompasses ameliorating or eliminating the physiological sequelae of the disease.

The term "ameliorate" in the context of this invention is understood as meaning any improvement on the situation of the patient treated.

The term "prevention" or "to prevent" in the context of this specification means administration of a compound or formulation according to the invention to reduce the risk of acquiring or developing the disease or one or more symptoms associated with said disease.

Pharmaceutical Forms

Topical administration of the aqueous pharmaceutical composition of the invention to the nasal cavities may be accomplished utilizing nasal spray devices such as a metered-dose spray pump or single- and duo-dose spray devices. Therefore, an aspect of the invention is directed to a nasal spray device comprising the aqueous pharmaceutical composition of the invention. In a preferred embodiment, the nasal spray comprising the aqueous pharmaceutical composition of the invention, is a metered-dose spray pump.

Solutions may be administered intranasally by inserting an appropriate device (such as a nasal spray bottle and actuator) into each nostril. Active drug is then expelled from the nasal spray device.

The following example is merely illustrative of certain embodiments of the invention and cannot be considered as restricting it in any way.

EXAMPLES

Materials and Methods
Materials
Bilastine was provided by Neuland Laboratories limited, Mometasone furoate monohydrate was provided by Sterling, hydroxypropyl-β-cyclodextrin was provided by Roquette, Polysorbate 80 by Seppic, MCC and Na-CMC by JRS Pharma, Citric Acid monohydrate by Brenntag, anhydrous glycerine was supplied by KLK Oleo, and Benzalkonium chloride and Trisodium citrate dihydrate were both supplied by Merck.

HPLC measurements were conducted using a HPLC-HCLASS Chromatographic System with PDA or UV-VIS detector equipped with a Xbridge Shield RP18 3.5 μm 4.6 μm×250 mm Column. Mobile phases were ammonium bicarbonate (10 mM pH 9, FLUKA), acetonitrile (FISCHER) and methanol (SCHARLAU). Samples were submitted to Acrodisc 32 mm Sryinge Filters with 1.2 μm Supor Membrane, Batch: 18-1077 (PALL).

Manufacture Technique of the Formulation

Aqueous pharmaceutical compositions belonging to the invention were prepared following the process:

Staqe I: Preparation of an Aqueous Solution of Bilastine

An aqueous solution of bilastine containing 4 mg/ml of bilastine and a volume of purified water was prepared.

Citric acid monohydrate is added to purified water to reach a pH of 4.45 and the solution was stirred to obtain a uniform and homogenous solution. Then, 2-hydroxipropyl-β-cyclodextrin (25 mg/ml) was added to the aqueous solution and the mixture was stirred to obtain a homogenous solution.

(2-[4-(2-{4-[1-(2-ethoxyethyl)-1H-benzimidazol-2-yl]-1-piperidinyl}ethyl)phenyl]-2-methylpropanoic acid) or bilastine was then added and the solution was stirred to obtain a homogenous solution. Benzalkonium chloride (preservative) was subsequently added to the aqueous solution of bilastine maintaining the stirring conditions. Further, a buffer agent (trisodium citrate dehydrate) was added maintaining the stirring conditions to reach a pH of 4.45 in the aqueous solution of bilastine.

Stage II: Preparation of a Dispersion of Mometasone

Polysorbate 80 was added to purified water under stirring. Then, Mometasone furoate monohydrate was added to the solution of Polysorbate 80 maintaining the stirring conditions for about 20 min.

Stage III: Preparation of an Aqueous Suspension of a Suspending Agent

An aqueous suspension of a suspending agent is prepared by adding Vivapur MCG 811P to purified water under stirring. The resulting aqueous suspension is then homogenized with high shear forces. The resulting aqueous suspension is left to rest for about 15 min.

Anhydrous glycerine is added to the aqueous suspension while stirring.

Stage IV: Combining the Solution Phase and the Suspension Phase to Obtain the Final Formulation.

Final Formulation:

The solution phase of bilastine was added on the suspension phase and homogenized by stirring. Then, the dispersion of mometasone furoate was added maintaining the conditions of stirring for around further 10 min. Purified water was added up to the total weight maintaining the conditions of stirring.

The pH of the composition was measured with pHmeter Crison Microph 2000 at room temperature, and when necessary trisodium citrate dehydrate was added to reach a pH of 4.6.

The homogeneity assessment was done by observing the sample and confirming the absence of phase separation or presence of agglomerates.

The following materials have been used: bilastine (provided by FAES Farma), furoato de mometasona (provided by Sterling), citric acid monohydrate (Brenntag), trisodium citrate dihydrate (Merck chemicals & life science), anhydrous glycerine (Brenntag), Tween 80 (Croda), Vivapur®

MCG (JRS PHARMA), benzalkonium chloride (Merk Millipore) and 2-hydroxypropyl-β-cyclodextrin (Roquette).

The water used in the following examples was purified water obtained using an Elix® water purification system from Merck-Millipore.

Example 1—Homogeneity De Visu Assessment Using HPBCD as a Solubilising Agent The formulation of this example was prepared as explained above. The table below shows the content of the components in the final formulation of this example of the invention:

| Component | mg/mL |
| --- | --- |
| Bilastine | 4 |
| Mometasone Furoate monohydrate | 0.517 |
| Citric acid monohydrate | 2 |
| Trisodium citrate dihydrate | q.s pH 4.6 |
| Anhydrous glycerine | 21 |
| Polysorbate 80 (Tween 80) | 0.1 |
| Microcrystalline cellulose and sodium carboxymethylcellulose (Vivapur MCG) | 18 |
| Benzalkonium chloride | 0.2 |
| Hydroxypropyl-β-cyclodextrin | 25 |
| Purified water | q.s. 1 mL |

*0.517 mg/mL of Mometasone furoate monohydrate are equivalent to 0.5 mg/mL of Mometasone furoate in anhydrous form.

Two further aqueous pharmaceutical compositions of the invention were prepared having the same compositions as in the above composition but changing the bilastine content to 2 mg/mL and to 8 mg/mL.

pH determination: 4.6

Homogeneity de visu assessment: the formulation was homogeneous.

Example 2—Comparative. Homogeneity De Visu Assessment Using Alternative Solubilizer Agents of Bilastine and Mometasone Five formulations wherein the cyclodextrin was replaced with alternative solubilizer agents of Bilastine and mometasone were prepared and their homogeneity de visu assessment was made. Formulas of the present example were prepared in a similar way as explained above but this time cyclodextrin was replaced with Labrasol® (8 g.), Brij® 35 (8 g.) (Fagron), Myrj® 40 (8 g.) (Fagron), Tween® 80 (8 g.) (Basf) or, Poloxamer 188 (10 g.) (Basf) respectively, due to their surfactant properties. In the formulations of the present example, Spam 80 acts as an antifoam agent.

2.1 Homogeneity De Visu Assessment Using Labrasol®.

Table below shows the exact content of the components in the final formulation of the present example using Labrasol® as a solubilizer agent of bilastine and mometasone:

| Component | % |
| --- | --- |
| Bilastine | 0.36 |
| Mometasone Furoate | 0.05 |
| Vivapur ® MCG | 1.25 |
| Labrasol ® | 3.6 |
| Sodium citrate hemihydrate | q.s pH 4.4 |
| Citric acid anhydrous | 0.18 |
| Deionized water | q.s 100 g |
| Tween 80 | 0.0075 |
| Glycerol | 1.8 |
| Benzalkonium chloride | 0.015 |
| Span 80 | 0.30 |

Homogeneity de visu assessment: there was a phase separation, thus the formulation was not homogeneous.

2.2 Homogeneity De Visu Assessment Using Myrj® 40.

Table below shows the exact content of the components in the final formulation of the present example using Myrj® 40 as a solubilizer agent of bilastine and mometasone:

| Component | % |
| --- | --- |
| Bilastine | 0.36 |
| Mometasone Furoate | 0.05 |
| Vivapur ® MCG | 1.25 |
| Myrj 40 | 3.6 |
| Sodium citrate hemihydrate | q.s pH 4.4 |
| Citric acid anhydrous | 0.18 |
| Deionized water | q.s 100 g |
| Tween 80 | 0.0075 |
| Glycerol | 1.8 |
| Benzalkonium chloride | 0.015 |
| Span 80 | 0.30 |

Homogeneity de visu assessment: a coagulated mass was formed at the bottom of the container, thus the formulation was not homogeneous.

2.3 Homogeneity De Visu Assessment Using Brij® 35.

Table below shows the exact content of the components in the final formulation of the present example using Brij® 35 as a solubilizer agent of bilastine and mometasone:

| Component | % |
| --- | --- |
| Bilastine | 0.36 |
| Mometasone Furoate | 0.05 |
| Vivapur ® MCG | 1.25 |
| Brij 35 | 3.6 |
| Sodium citrate hemihydrate | q.s pH 4.4 |
| Citric acid anhydrous | 0.18 |
| Deionized water | q.s 100 g |
| Tween 80 | 0.0075 |
| Glycerol | 1.8 |
| Benzalkonium chloride | 0.015 |
| Span 80 | 0.30 |

Homogeneity de visu assessment: there was a significant amount of foam, thus the formulation was not homogeneous.

2.4 Homogeneity De Visu Assessment Using Tween 80.

Table below shows the exact content of the components in the final formulation of the present example using Tween 80 as a solubilizer agent of bilastine and mometasone:

| Component | % |
| --- | --- |
| Bilastine | 0.36 |
| Mometasone Furoate | 0.05 |
| Vivapur ® MCG | 1.25 |
| Tween 80 | 0.0075 |
| Sodium citrate hemihydrate | q.s pH 4.4 |
| Citric acid anhydrous | 0.18 |
| Deionized water | q.s 100 g |

-continued

| Component | % |
|---|---|
| Glycerol | 1.8 |
| Benzalkonium chloride | 0.015 |
| Span 80 | 0.30 |

Homogeneity de visu assessment: there was a phase separation, thus the formulation was not homogeneous.

2.5 Homogeneity De Visu Assessment Using Poloxamer 188.

Table below shows the exact content of the components in the final formulation of the present example using Poloxamer 188 as a solubilizer agent of bilastine and mometasone:

| Component | % |
|---|---|
| Bilastine | 0.36 |
| Mometasone Furoate | 0.05 |
| Vivapur ® MCG | 1.25 |
| Poloxamer 188 | 4.5 |
| Sodium citrate hemihydrate | q.s pH 4.4 |
| Citric acid anhydrous | 0.18 |
| Deionized water | q.s 100 g |
| Tween 80 | 0.0075 |
| Glycerol | 1.8 |
| Benzalkonium chloride | 0.015 |
| Span 80 | 0.30 |

Homogeneity de visu assessment: there was a phase separation, thus the formulation was not homogeneous.

Example 3. Solubility of Bilastine and Mometasone Furoate Monohydrate Formulations Using Amounts of HPBCD from 12.5 to 100 mg/mL at pH Values of 4.3, 4.6 and 4.9

Six different formulations (with mometasone furoate monohydrate and the rest of excipients as defined in example 2) were prepared (see table below). The six formulations had amounts of HPBCD from 12.5 to 100 mg/mL. Then, in each of them an excessive amount of bilastine was added and the maximum solubility was tested. Furthermore, the percentage of the mometasone furoate dissolved was also tested. All the measurements were conducted at time 0.

| Formulation (HPBCD concentration) | pH | Solubility Mometasone (mg/mL) | % Mometasone dissolved in the drug product | Solubility Bilastine (mg/mL) |
|---|---|---|---|---|
| 1 (12.5 mg/mL) | 4.3 | 0.003 | 0.6% | 4.3 |
| | | 0.003 | 0.6% | 4.3 |
| | 4.6 | 0.003 | 0.6% | 4.5 |
| | | 0.003 | 0.6% | 4.6 |
| | 4.9 | 0.003 | 0.6% | 4.8 |
| | | 0.003 | 0.6% | 4.8 |
| 2 (18.75 mg/mL) | 4.3 | 0.005 | 1.0% | 4.3 |
| | | 0.005 | 1.0% | 4.3 |
| | 4.6 | 0.005 | 1.0% | 4.6 |
| | | 0.005 | 1.0% | 4.6 |
| | 4.9 | 0.005 | 1.0% | 4.8 |
| | | 0.005 | 1.0% | 4.9 |
| 3 (25 mg/mL) | 4.3 | 0.006 | 1.2% | 12.0 |
| | | 0.006 | 1.2% | 11.9 |
| | 4.6 | 0.007 | 1.4% | 9.6 |
| | | 0.006 | 1.2% | 9.8 |
| | 4.9 | 0.006 | 1.2% | 8.0 |
| | | 0.007 | 1.4% | 8.1 |
| 4 (50 mg/mL) | 4.3 | 0.016 | 3.2% | 16.1 |
| | | 0.013 | 2.6% | 16.0 |
| | 4.6 | 0.015 | 3.0% | 13.1 |
| | | 0.016 | 3.2% | 13.6 |
| | 4.9 | 0.017 | 3.4% | 12.4 |
| | | 0.015 | 3.0% | 6.2(*) |
| 5 (75 mg/mL) | 4.3 | 0.019 | 3.8% | 19.4 |
| | | 0.020 | 4.0% | 19.7 |
| | 4.6 | 0.021 | 4.2% | 17.2 |
| | | 0.020 | 4.0% | 17.4 |
| | 4.9 | 0.023 | 4.6% | 15.1 |
| | | 0.022 | 4.4% | 15.2 |
| 6 (100.25 mg/mL) | 4.3 | 0.030 | 6.0% | 22.9 |
| | | 0.029 | 5.8% | 20.9 |
| | 4.6 | 0.032 | 6.4% | 13.7(*) |
| | | 0.031 | 6.2% | 20.8 |
| | 4.9 | 0.032 | 6.4% | 18.2 |
| | | 0.032 | 6.4% | 18.1 |

(*)A difference between the grams needed to reach saturation in the sample in respect of its corresponding replicate was observable.

The results are represented in FIG. 1 in graphs A and B therein. The results show that the desired solubility for the bilastine dosage of 8 mg/mL in the tested pH range of 4.3-4.9 is reached when using at least 25 mg/mL of HPBCD at time 0. The results also show that when increasing the content of HPBCD in the tested pH range of 4.3-4.9, the content of solubilized steroid is also increased (see table above and FIG. 1 in graph B therein.

Example 4—Comparative. Solubility of Bilastine and Mometasone Furoate Monohydrate Formulations Using Amounts of Kolliphor RH40 from 0 to 50 mg/mL at pH Values of 3.7, 4.0, 4.3 and 4.6

Kolliphor RH40 (Macrogolglycerol hydroxystearate), a non-ionic oil-in-water solubilizing and emulsifying agent, derived from hydrogenated castor oil and ethylene oxide, was evaluated as solubilizer agent of bilastine and mometasone.

To this end, aqueous formulations of Kolliphor RH40 at concentrations 0, 5, 15, 25 and 50 mg/mL and at pH values of 3.7, 4.0, 4.3 and 4.6 were prepared.

To each of the solubilizer formulations, bilastine was added until saturation was observed in order to determine the maximum concentration of bilastine.

Figure 3:
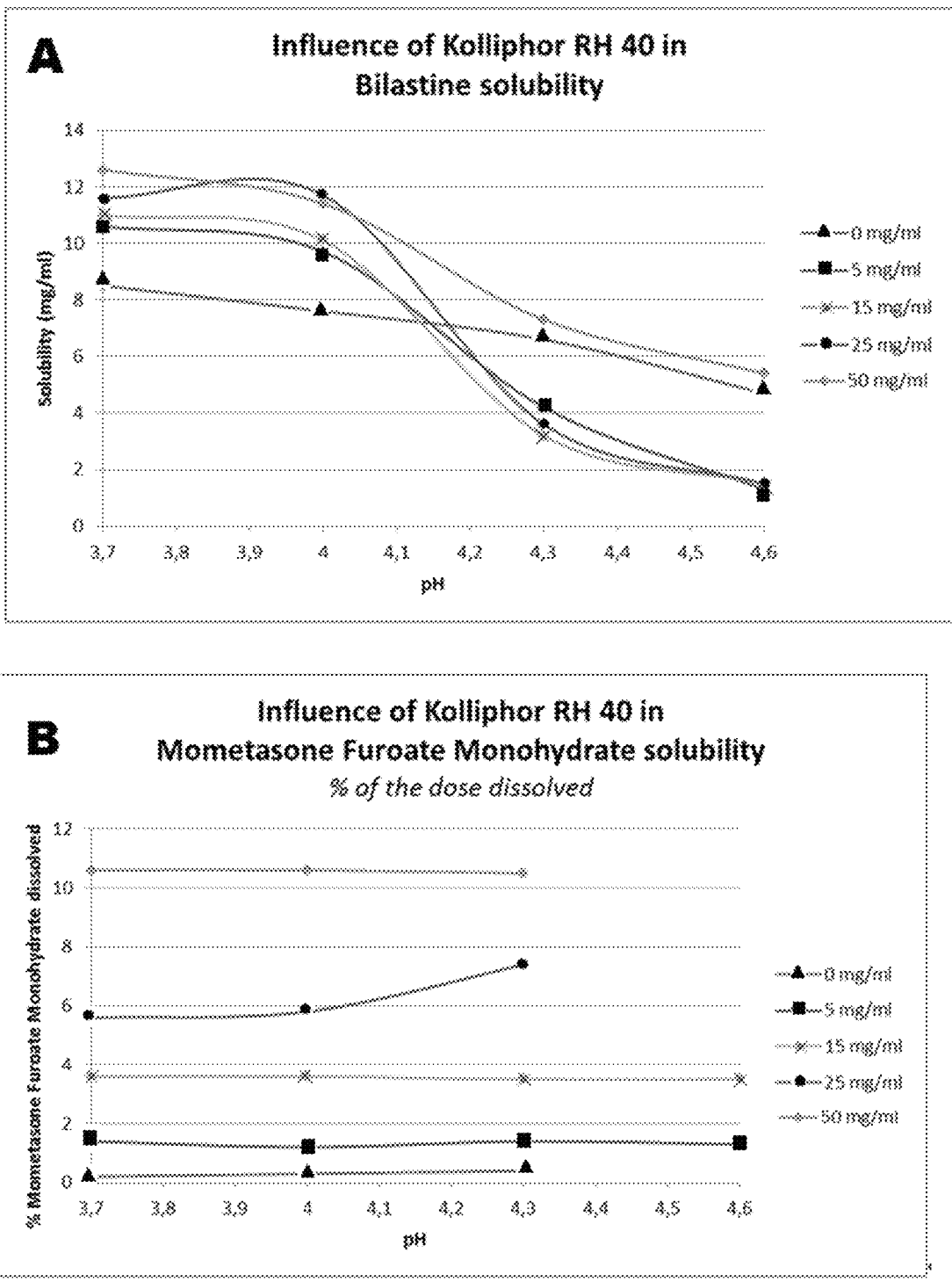
FIG. 3 in graph A therein shows the influence of kolliphor RH40 in the solubility of bilastine.

Additionally, 0.5 mg/mL of mometasone furoate monohydrate was added to each formulation. The influence of Kolliphor RH40 in bilastine solubility is represented in FIG. 3 in graphs A and B therein. It is shown that, at pH values above 4.3, Kolliphor RH40 at a concentration of 50 mg/mL is insufficient in solubilizing 8 mg/mL of Bilastine (FIG. 3 in graph A therein. In addition, at the concentration of 50 mg/mL and pH of 4.3, Kolliphor RH40 solubilizes more than 10% of the added mometasone furoate monohydrate (FIG. 3 in graph B therein.

The results demonstrate that Kolliphor RH40 is an inadequate solubilizer in the context of the present invention since it does not properly solubilize the desired amount of bilastine while simultaneously solubilizes a significant amount of mometasone furoate monohydrate.

Example 5—Comparative, Stability Using Kolliphor RH40

A comparative formulation wherein the cyclodextrin is replaced with Kolliphor RH40 as solubilizer agent was prepared.

The formulation of the present example was prepared in a similar way as explained above but this time cyclodextrin was replaced with Macrogolglycerol hydroxystearate (Kolliphor RH40) and the quantities of the components was slightly adapted. The table below shows the exact content of the components in the final formulation of the present example:

| Component | mg/mL |
|---|---|
| Bilastine | 4 |
| Mometasone Furoate monohydrate | 0.517 |
| Citric acid monohydrate | 2.19 |
| Trisodium citrate dihydrate | q.s pH 5 |
| Anhydrous glycerine | 20 |
| Polysorbate 80 (Tween 80) | 0.1 |
| Microcrystalline cellulose and sodium carboxymethylcellulose (Vivapur MCG) | 13.1 |
| Benzalkonium chloride | 0.3 |
| Macrogolglycerol hydroxystearate (Kolliphor RH40) | 50 |
| Sorbitan Monooleate (Span 80) | 6 |
| Purified water | q.s. 1 mL |

*0.517 mg/mL of Mometasone furoate monohydrate are equivalent to 0.5 mg/mL of Mometasone furoate in anhydrous form.

In the formulation of the present example, sorbitan monooleate acts as an antifoam agent. A batch manufactured according to the table above was prepared, packaged and placed in stability chambers wherein the conditions were 25° C./40% RH and 40° C./25% RH for the duration of 3 months.

| Total degradation products % w/w | T0 | 25° C. 40% RH | 40° C. 25% RH |
|---|---|---|---|
| Mometasone Furoate monohydrate | 0.15% | 0.31% | 0.33% |

The results show that the level of mometasone total degradation products is over pharmaceutical acceptable levels. Moreover, the content of mometasone total degradation products increases over time, since its value is doubled from time 0 to 3 months at both stability conditions, 25° C./40% RH and 40° C./25% RH. The stability of the formula with Kolliphor RH40 as solubilizer agent is considered unsatisfactory. Thus it is concluded that Kolliphor RH40 is not adequate for solubilizing bilastine because not only it does not solubilize enough bilastine (see example above) but it has the unwanted side effect of leading to the degradation of mometasone over pharmaceutical acceptable levels.

Example 6—Stability Using Cyclodextrin

Three different Bilastine formulas with 2, 4 and 8 mg/mL were prepared in a similar way as explained above and placed into stability chambers. The table below shows the exact content of the components in the three formulas of the present example:

| Component | mg/mL | | |
|---|---|---|---|
| Bilastine | 2 | 4 | 8 |
| Mometasone Furoate monohydrate | 0.517 [1] | 0.517 [1] | 0.517 [1] |
| Citric acid monohydrate | 2.0 | 2.0 | 2.0 |
| HPBCD | 25 | 25 | 25 |
| Anhydrous glycerine | 21 | 21 | 21 |
| Polysorbate 80 (Tween 80) | 0.1 | 0.1 | 0.1 |
| Microcrystalline cellulose and sodium carboxymethylcellulose (Vivapur MCG) | 18 | 18 | 18 |
| Benzalkonium chloride | 0.2 | 0.2 | 0.2 |
| Trisodium citrate dihydrate | 1.65 q.s pH 4.6 | 1.65 q.s pH 4.6 | 1.65 q.s pH 4.6 |
| Purified water | q.s 1 mL | q.s 1 mL | q.s 1 mL |

[1] 0.517 mg/ml of Mometasone furoate monohydrate are equivalent to 0.5 mg/ml of Mometasone in its anhydrous form.

The three formulas (bilastine at a concentration of 2, 4 and 8 mg/mL) were placed in stability chambers wherein the conditions were 25° C./40% RH and 40° C./25% RH for the duration of 6 or 12 months.

| Total degradation products % w/w | T0 | 40° C. 25% RH 3 months | 40° C. 25% RH 6 months | 25° C. 40% RH 9 months | 25° C. 40% RH 12 months |
|---|---|---|---|---|---|
| Bilastine 2 mg/mL | | | | | |
| Mometasone Furoate | 0.05% | 0.15% | 0.20% | 0.05% | 0.05% |
| Bilastine 4 mg/mL | | | | | |
| Mometasone Furoate | 0.05% | 0.14% | 0.18% | 0.05% | 0.05% |
| Bilastine 8 mg/mL | | | | | |
| Mometasone Furoate | 0.05% | 0.14% | 0.17% | 0.05% | 0.05% |

As can be seen in the tables above, a slightly increase in the level of mometasone total degradation products is found after 6 months at 40° C./25% RH. This increase is almost the same for the three formulas of the example. This increase is not noticed after 12 months at 25° C./40% RH. Thus, the stability of the three formulas is considered satisfactory and pharmaceutically acceptable.

These results, when compared to those obtained in comparative example 4 show that contrary to Kolliphor RH40, the cyclodextrin HPBCD is sufficient to solubilize 8 mg/mL of bilastine without the unwanted side effects of degradation of mometasone over pharmaceutical acceptable levels.

Example 7—Mometasone Impurities

This example shows the data produced by the inventors upon the surprising discovery that there are mometasone impurities originating from the presence of HPBCD as solubilizer.

The percentage of Mometasone was calculated-using the following formula:

$$\% \text{Mometasone} = \frac{Am \times Pstd \times Dm \times F \times d}{Astd \times Dstd \times Pm \times T} \times 100$$

Where:
Am: Area of Mometasone peak in sample solution.
Astd: Mean of peak areas of Mometasone (n=5) in STD1 Solution A
Pstd: Weight of Mometasone in the standard solution (mg)
Pm: Weight of sample (g)
Dstd: Dilution of the Mometasone in the standard solution (mL)
Dm: Dilution of sample solution (mL)
F: Potency of the Mometasone working or reference standard (amount per one)
T: Theoretic quantity of Mometasone in suspension (mg/mL) (0.517 mg/mL)
d: Density of sample (g/mL)
The percentage of Mometasone degradation products was calculated using the following formula:

$$\% \text{ Impurity} = \frac{Am \times Pstd \times Dm \times F \times d}{Astd \times Dstd \times Pm \times T \times RRF} \times 100$$

Where:
Am: Area of Mometasone peak in sample solution.
Astd: Mean of peak areas of Mometasone (n=5) in STD1 Solution B
Pstd: Weight of Mometasone in the standard solution (mg)
Pm: Weight of sample (g)
Dstd: Dilution of the Mometasone in the standard solution (mL)
Dm: Dilution of sample solution (mL)
F: Potency of the Mometasone working or reference standard (amount per one)
T: Theoretic quantity of Mometasone in suspension (mg/mL) (0.517 mg/mL)
d: Density of sample (g/mL)
RRF: Relative Response Factor of Mometasone degradation product (considered as 1).

To evaluate the influence that the cyclodextrin HPBCD had on the impurities of mometasone, formulations similar to the one described in example 1 (see table therein) were studied at pH 4.6 for increasing cyclodextrin concentrations of from 25 to 95 mg/mL. The formulations were submitted to forced stability conditions at 50° C. for a 3-month period. The results were obtained from HPLC measurements.

| HPBCD concentration | Dissolved mometasone (%) | Mometasone impurities (%) |
|---|---|---|
| 25 mg/mL | 0.7 | 0.2 |
| 50 mg/mL | 3.0 | 0.7 |
| 65 mg/mL | 5.2 | 1.0 |
| 85 mg/mL | 7.2 | 1.3 |
| 95 mg/mL | 10.5 | 1.9 |

Figure 4A:
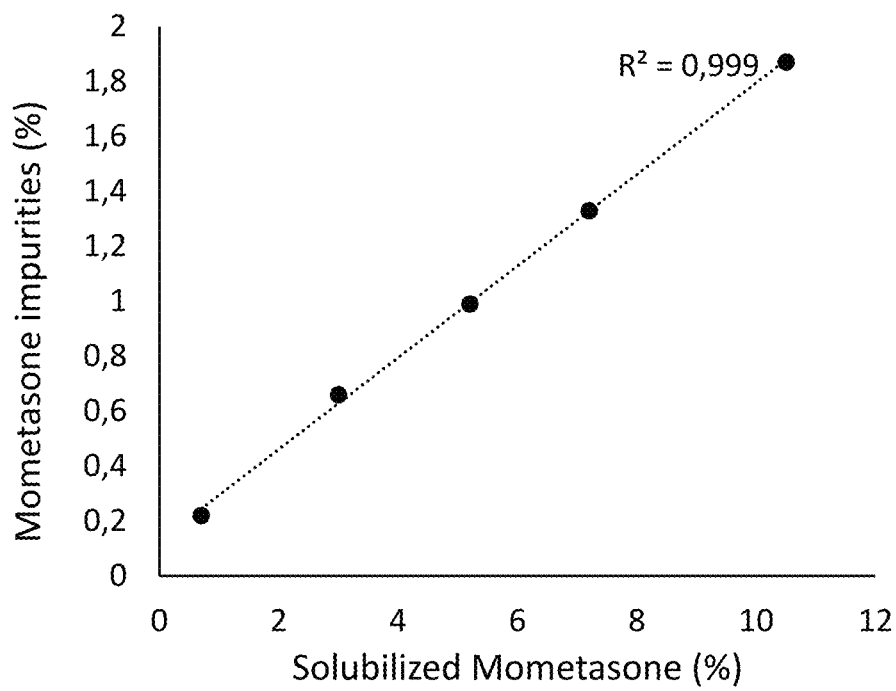
FIG. 4A shows that there is a linear behaviour between the percentage of dissolved mometasone and the percentage of mometasone impurities.

The plot of mometasone impurities against solubilized mometasone reveals that there is a direct linear relation between these two parameters, as shown in FIG. 4A.

Figure 4B:
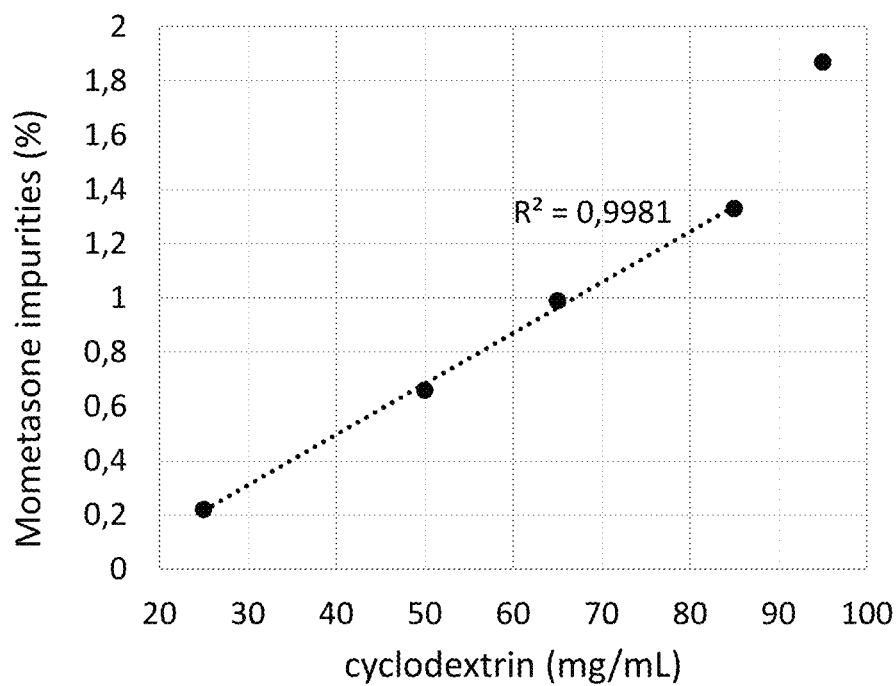
FIG. 4B shows that the HPBCD cyclodextrin minimizes the solubilisation of mometasone when used at a concentration lower than 85 mg/mL.

The plot of mometasone impurities against cyclodextrin concentration is represented in FIG. 4B. A steady increase in the percentage of mometasone impurities is observed with the increase of HPBCD concentration, in the interval 25-85 mg/mL of cyclodextrin. When the cyclodextrin concentration is increased to 95 mg/mL, the trend is no longer linear and a significant increase in the mometasone impurities is observed.

The invention claimed is:

1. An aqueous pharmaceutical composition comprising:
   a) bilastine or a pharmaceutically acceptable salt or solvate thereof,
   b) mometasone or a pharmaceutically acceptable derivative thereof selected from an ester, ether and ketonide derivative,
   c) a suspending agent,
   d) 2-hydroxypropyl-β-cyclodextrin;
   wherein the pH of the aqueous pharmaceutical composition is between 3.5 and 5.5, and
   wherein the content of 2-hydroxypropyl-β-cyclodextrin is less than 8.5% by weight.

2. The aqueous pharmaceutical composition according to claim 1, wherein the content of bilastine or a pharmaceutically acceptable salt or solvate thereof is comprised between 0.2 wt % and 0.8 wt. %.

3. The aqueous pharmaceutical composition according to claim 1, wherein the component b) is mometasone furoate.

4. The aqueous pharmaceutical composition according to claim 1, wherein the content of 2-hydroxypropyl-β-cyclodextrin is less than 5 wt. %.

5. The aqueous pharmaceutical composition according to claim 1, wherein the content of 2-hydroxypropyl-β-cyclodextrin is comprised between 1 and 5 wt. %.

6. The aqueous pharmaceutical composition according to claim 1, wherein the pH in the aqueous pharmaceutical composition is between 4.0 and 5.0.

7. The aqueous pharmaceutical composition according to claim 1, wherein the suspending agent is selected from cellulose, cellulose derivatives selected from cellulose ether derivatives, or a mixture thereof, wherein the hydroxyl groups of cellulose have been partially or fully substituted to provide cellulose ethers.

8. A process for preparing an aqueous pharmaceutical composition according to claim 1, comprising:
   a) preparing an aqueous solution of 2-hydroxypropyl-β-cyclodextrin, wherein the content of 2-hydroxypropyl-β-cyclodextrin is less than 8.5% by weight,
   b) adding bilastine or a pharmaceutically acceptable salt or solvate thereof, to the aqueous solution of step a), and adding a buffer agent to obtain an aqueous solution of bilastine having a pH of between 3.5 and 5.5,
   c) preparing a dispersion of mometasone, or a pharmaceutically acceptable derivative thereof selected from an ester, ether and ketonide derivative with a surfactant in purified water,
   d) preparing an aqueous suspension of a suspending agent,
   e) adding the aqueous solution of step b) to the aqueous suspension of step d), and subsequently adding the dispersion of mometasone from step c), and homogenizing the mixture under stirring.

9. The process according to claim 8, further comprising adding a buffer agent in the aqueous solution of step a), step b), or both.

10. The process according to claim 8, wherein the aqueous solution of 2-hydroxypropyl-β-cyclodextrin is an aqueous solution wherein the content of 2-hydroxypropyl-β-cyclodextrin is less than 5% by weight.

11. A nasal spray device comprising the aqueous pharmaceutical composition according to claim 1.

12. The aqueous pharmaceutical composition according to claim 1, wherein the pH in the aqueous pharmaceutical composition is between 4.3 and 4.9.

13. The process according to claim 9, wherein step e) further comprises adding a buffer to reach a pH of between 3.5 and 5.5.

14. A method for the treatment and/or prevention of a disorder or disease susceptible to amelioration by antagonism of $H_1$ histamine receptor and/or a corticosteroid-responsive disease, comprising administering an effective amount of an aqueous pharmaceutical composition according to claim 1.

15. The method according to claim 14, wherein the disorder or disease susceptible to amelioration by antagonism of $H_1$ histamine receptor is an allergic disorder or disease selected from rhinitis, conjunctivitis and rhinoconjunctivitis.

16. The method according to claim 14, wherein the corticosteroid-responsive disease is selected from asthma, allergic and non-allergic rhinitis, non-malignant proliferative and inflammatory diseases.

17. The aqueous pharmaceutical composition according to claim 1, wherein the content of 2-hydroxypropyl-β-cyclodextrin is between 1% and 8.5% by weight.

18. The aqueous pharmaceutical composition according to claim 1, wherein the content of bilastine or a pharmaceutically acceptable salt or solvate thereof is comprised between 0.3 and 0.8 wt. %.

19. The aqueous pharmaceutical composition according to claim 1, wherein the content of mometasone or a pharmaceutically acceptable derivative thereof selected from an ester, ether and ketonide derivative, is comprised between 0.02 and 0.06 wt. %.

* * * * *

UNITED STATES PATENT AND TRADEMARK OFFICE
CERTIFICATE OF CORRECTION

PATENT NO. : 11,642,309 B2
APPLICATION NO. : 16/756112
DATED : May 9, 2023
INVENTOR(S) : Gonzalo Hernandez Herrero et al.

It is certified that error appears in the above-identified patent and that said Letters Patent is hereby corrected as shown below:

In the Specification

Column 2, Line 50, "2-hydroxypropyl-p-cyclodextrin" should be
-- 2-hydroxypropyl-β-cyclodextrin --.

Column 2, Lines 53-54, "β-hydroxypropyl-p-cyclodextrin" should be
-- 2-hydroxypropyl-β-cyclodextrin --.

Column 2, Lines 65-66, "2-hydroxypropyl-p-cyclodextrin" should be
-- 2-hydroxypropyl-β-cyclodextrin --.

Column 2, Lines 66-67, "2-hydroxypropyl-p-cyclodextrin" should be
-- 2-hydroxypropyl-β-cyclodextrin --.

Column 9, Line 65, "0.026 wt. 30%" should be -- 0.026 wt. % --.

Signed and Sealed this
Twenty-seventh Day of June, 2023

Katherine Kelly Vidal
*Director of the United States Patent and Trademark Office*